US00PP21690P2

(12) United States Plant Patent
Lowe

(10) Patent No.: US PP21,690 P2
(45) Date of Patent: Feb. 1, 2011

(54) ***GERANIUM* PLANT NAMED 'MELODY'**

(50) Latin Name: *Geranium cinereum*
Varietal Denomination: Melody

(75) Inventor: Carl Marius Lowe, Holsworthy (GB)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/590,824

(22) Filed: Nov. 14, 2009

(51) Int. Cl.
*A01H 5/00* (2006.01)

(52) U.S. Cl. ..... Plt./324

(58) Field of Classification Search ..... Plt./324
See application file for complete search history.

(56) References Cited

U.S. PATENT DOCUMENTS

PP8,006 P * 10/1992 Hofmann ..... Plt./325

OTHER PUBLICATIONS

UPOV ROM GTITM Computer Database, GTI Jouve Retrieval Software 2010/3 Citation for 'Melody'.*

* cited by examiner

*Primary Examiner*—Wendy C. Haas
(74) *Attorney, Agent, or Firm*—C. A. Whealy

(57) ABSTRACT

A new and distinct cultivar of *Geranium* plant named 'Melody', characterized by its upright and outwardly spreading plant habit; strong growth habit; freely basal branching habit; freely flowering habit; red purple-colored flowers; and good garden performance.

2 Drawing Sheets

Botanical designation: *Geranium cinereum.*
Cultivar denomination: 'MELODY'.

BACKGROUND OF THE INVENTION

The present invention relates to a new and distinct cultivar of *Geranium* plant, botanically known as *Geranium cinereum,* and hereinafter referred to by the name 'Melody'.

The new *Geranium* plant originated from a cross-pollination during the summer of 2006 of two unnamed selections of *Geranium cinereum,* not patented. The new *Geranium* plant was discovered and selected by the Inventor as a single flowering plant from within the progeny of the stated cross-pollination grown in a controlled environment in Holsworthy, Devon, United Kingdom during the summer of 2008.

Asexual reproduction of the new *Geranium* plant by softwood cuttings in a controlled environment in Holsworthy, Devon, United Kingdom since the summer of 2008, has shown that the unique features of this new *Geranium* plant are stable and reproduced true to type in successive generations.

SUMMARY OF THE INVENTION

Plants of the new *Geranium* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Melody'. These characteristics in combination distinguish 'Melody' as a new and distinct cultivar of *Geranium:*

1. Upright and outwardly spreading plant habit.
2. Strong growth habit.
3. Freely basal branching habit.
4. Freely flowering habit.
5. Red purple-colored flowers.
6. Good garden performance.

Plants of the new *Geranium* differ primarily from plants of the parent selections primarily in flower color.

Plants of the new *Geranium* can be compared to plants of the *Geranium cinereum* 'Carol', disclosed in U.S. Plant Pat. No. 14,124. In side-by-side comparisons conducted in Holsworthy, Devon, United Kingdom, plants of the new *Geranium* differed primarily from plants of 'Carol' in flower color as plants of 'Carol' had purple-colored flowers.

BRIEF DESCRIPTION OF THE PHOTOGRAPHS

The accompanying colored photographs illustrate the overall appearance of the new *Geranium* plant, showing the colors as true as it is reasonably possible to obtain in colored reproductions of this type. Colors in the photographs may differ slightly from the color values cited in the detailed botanical description which accurately describe the colors of the new *Geranium* plant.

The photograph on the first sheet comprises a side perspective view of a typical flowering plant of 'Melody' grown in a container.

The photograph at the top of the second sheet is a close-up view of typical flowers of 'Melody'.

The photograph at the bottom of the second sheet is a close-up view of typical leaves of 'Melody'.

DETAILED BOTANICAL DESCRIPTION

The aforementioned photographs and following observations, measurements and values describe plants grown in Lisserbroek, The Netherlands in 13-cm containers in an outdoor nursery during the early summer. During the production of the plants, day temperatures ranged from 14° C. to 25° C. and night temperatures ranged from 4° C. to 15° C. Plants were one year old when the photographs and the description were taken. In the detailed description, color references are made to The Royal Horticultural Society Colour Chart, 2007 Edition, except where general terms of ordinary dictionary significance are used.

Botanical classification: *Geranium cinereum* 'Melody'.

Parentage:

*Female, or seed, parent.*—Unnamed selection of *Geranium cinereum,* not patented.

*Male or pollen parent.*—Unnamed selection of *Geranium cinereum,* not patented.

Propagation:

*Type.*—By softwood cuttings.

*Time to initiate roots.*—About one month at temperatures of 22° C. to 30° C.

*Time to produce a rooted young plant.*—About three months at temperatures of 14° C. to 30° C.

*Root description.*—Medium in thickness, moderately fibrous; greyed white in color.

*Rooting habit.*—Moderate branching; moderately dense.

Plant description:

*General appearance.*—Herbaceous perennial; upright and outwardly spreading plant habit; flattened globular in shape.

Growth and branching habit.—Moderately vigorous growth habit; freely basal branching habit with about eleven lateral branches developing per plant.

*Plant height, to top of umbels.*—About 16.7 cm.

*Plant width.*—About 34.2 cm.

*Lateral branches.*—Length: About 17.1 cm. Diameter: About 2 mm. Internode length: About 4.5 cm. Texture: Densely pubescent. Strength: Moderately strong. Color: Close to 145B.

Foliage description:

*Arrangement.*—Alternate; simple.

*Length, basal leaves.*—About 2.2 cm.

*Length, stem leaves.*—About 1.4 cm.

*Width, basal leaves.*—About 2.4 cm.

*Width, stem leaves.*—About 1.5 cm.

*Shape, basal and stem leaves.*—Orbicular.

*Apex, basal and stem leaves.*—Acute.

*Base, basal and stem leaves.*—Hastate.

*Margin, basal leaves.*—Palmately cleft; lobes crenate.

*Margin, stem leaves.*—Palmately cleft to parted; lobes entire.

*Venation pattern, basal and stem leaves.*—Palmate.

*Texture, upper and lower surfaces, basal and stem leaves.*—Moderately pubescent.

*Color, basal and stem leaves.*—Developing leaves, upper surface: Close to 137B. Developing leaves, lower surface: Close to 138B. Fully developed leaves, upper surface: Close to 137A to 137B; venation, close to 144B. Fully developed leaves, lower surface: Close to 138B; venation, close to 144C.

*Petiole.*—Length, basal leaves: About 7.2 cm. Length, stem leaves: About 1.6 cm. Diameter, basal leaves: About 1 mm. Diameter, stem leaves: About 0.8 mm. Texture, upper and lower surfaces, basal and stem leaves: Pubescent. Color, upper and lower surfaces, basal and stem leaves: Close to 144C.

Flower description:

*Flower arrangement.*—Single rotate flowers arranged in pairs arising from apical leaf axils; flowers face upright to slightly outward.

*Fragrance.*—None detected.

*Quantity of flowers.*—Freely flowering habit; about twelve flower buds and open flowers per lateral branch.

*Flowering season.*—In The Netherlands, flowering is continuous from late spring to late summer.

*Flower longevity.*—Flowers last about one week on the plant; flowers not persistent.

*Flower diameter.*—About 2.6 cm.

*Flower depth* (*height*).—About 1.2 cm.

*Flower buds.*—Length: About 8 mm. Diameter: About 4.5 mm. Shape: Elliptic. Texture: Densely pubescent. Color: Close to 147B.

*Petals.*—Quantity per flower: Five in a single whorl. Length: About 1.6 cm. Width: About 1.4 cm. Shape: Obcordate. Apex: Emarginate. Base: Attenuate. Margin: Entire. Texture, upper and lower surfaces: Mostly smooth; towards the base, densely pubescent. Color: When opening, upper surface: Close to 63A; towards the base, close to N79A; venation, close to N79A. When opening, lower surface: Close to 63B; towards the base, close to N79A to N79B; venation, close to N79A to N79B. Fully opened, upper surface: Close to 63B; towards the base, close to N79A; venation, close to N79A. Fully opened, lower surface: Close to 63B; towards the base, close to N79A to N79B; venation, close to N79A to N79B.

*Sepals.*—Quantity per flower: Five, arranged in a single whorl. Length: About 8 mm. Width: About 4 mm. Shape: Elliptic. Apex: Mucronate. Base: Cuneate. Margin: Entire. Texture, upper and lower surfaces: Densely pubescent. Color: When opening, upper surface: Close to 143A to 143B. When opening, lower surface: Close to 137C. Fully opened, upper surface: Close to 143A to 143B. Fully opened, lower surface: Close to 138A to 138B.

*Pedicels.*—Length: About 3.3 cm. Diameter: About 1 mm. Strength: Moderately strong. Angle: Erect to about 30° C. from vertical. Texture: Pubescent. Color: Close to 177C.

*Reproductive organs.*—Androecium: Stamen quantity per flower: About ten. Filament length: About 3 mm. Filament color: Close to N186C. Anther length: About 1.75 mm. Anther width: About 1 mm. Anther shape: Oblong. Anther color: Close to 202A. Pollen amount: None observed. Gynoecium: Pistil quantity per flower: One. Pistil length: About 5 mm. Stigma shape: Five-parted; reflexed. Stigma color: Close to N186C. Style length: About 3.5 mm. Style color: Close to 148B to 148C. Ovary color: Close to 144B to 144C.

*Seeds/fruits.*—Seed and fruit development have not been observed.

Disease/pest resistance: Plants of the new *Geranium* have not been observed to be resistant to pathogens and pests common to *Geraniums.*

Garden performance: Plants of the new *Geranium* have exhibited good garden performance and to tolerate rain and wind and have been observed to be suitable for USDA Zone 5 and tolerate high temperatures of about 35° C.

It is claimed:

1. A new and distinct *Geranium* plant named 'Melody' as illustrated and described.

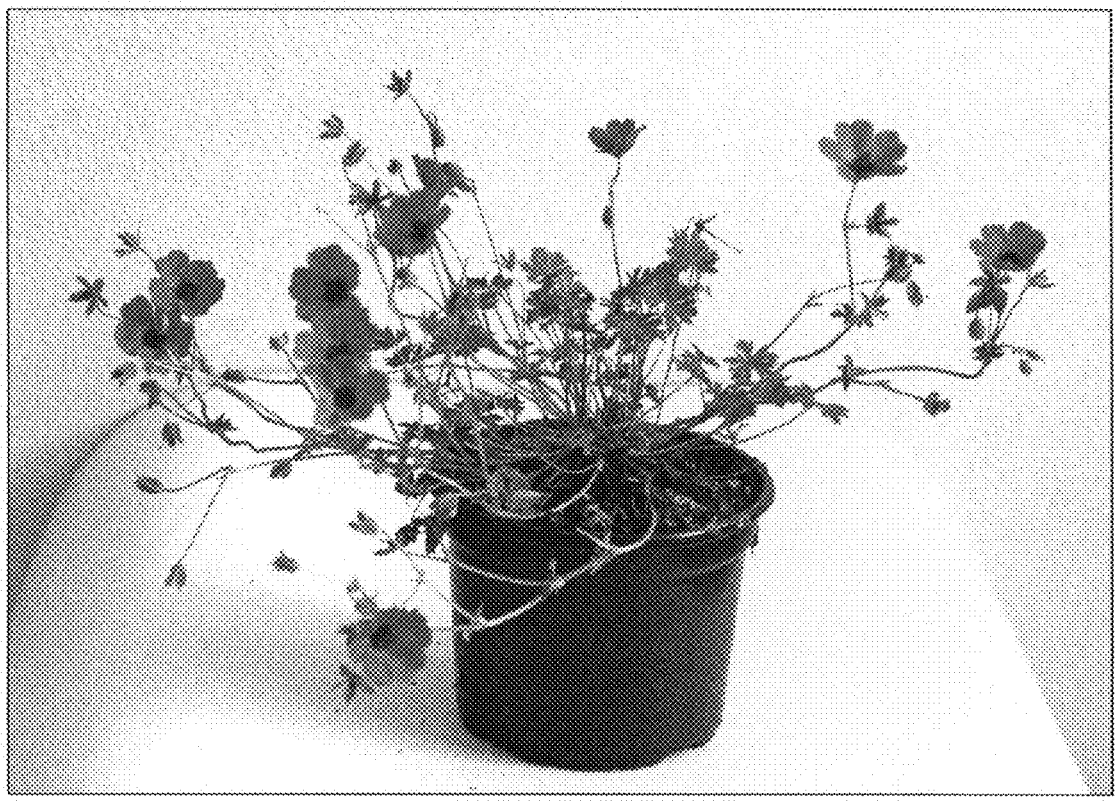

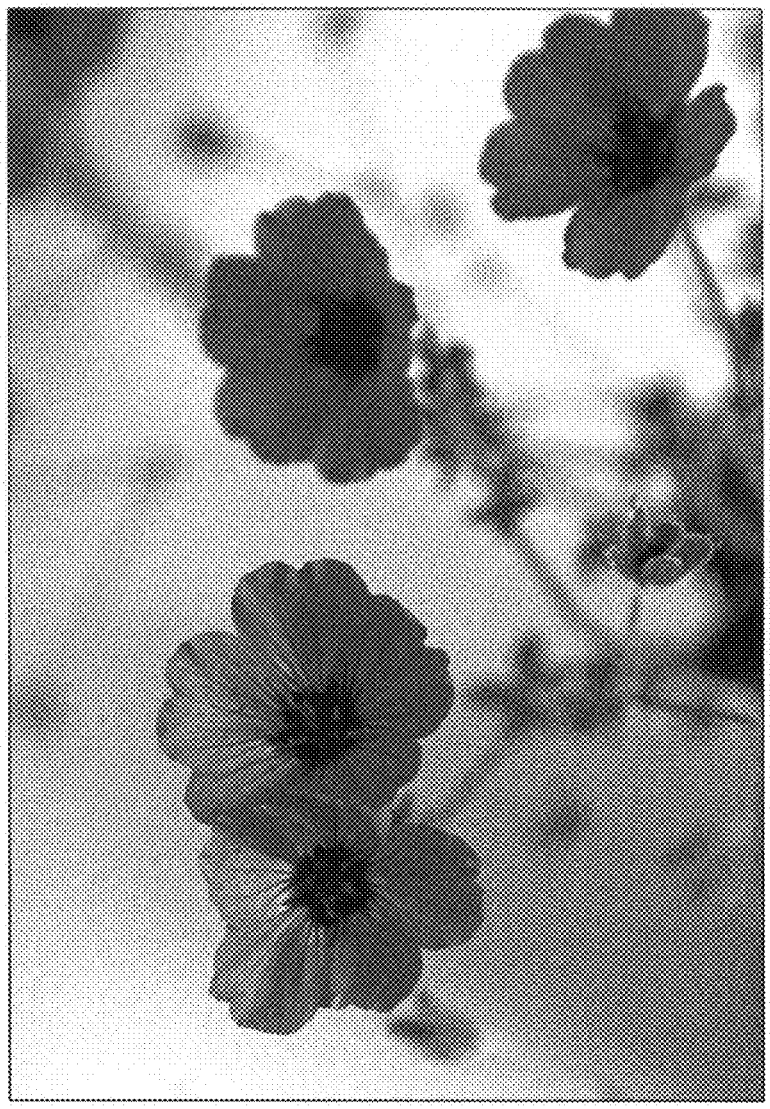
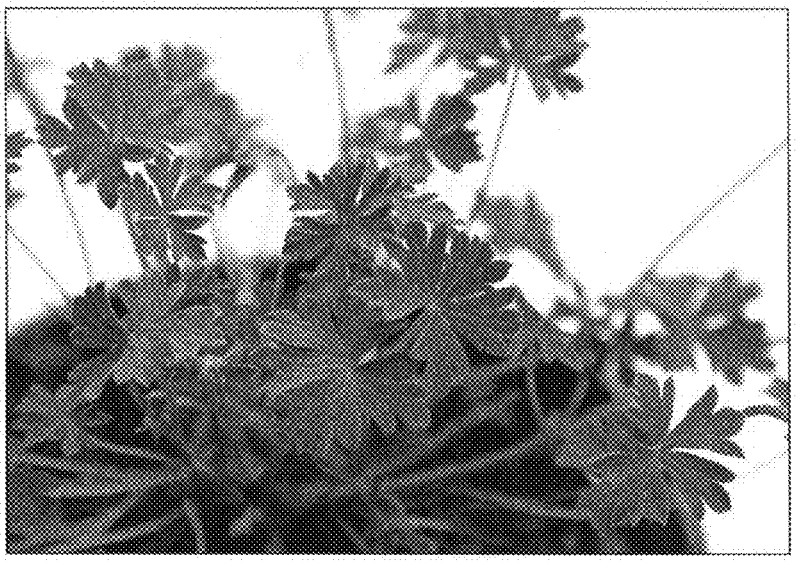

* * * * *